United States Patent [19]

Chaikin et al.

[11] 4,207,244

[45] Jun. 10, 1980

[54] PROCESS FOR SEPARATION OF WOOL WAX FROM FATS IN WOOL GREASE OR MIXTURES CONTAINING WOOL GREASE

[75] Inventors: Malcolm Chaikin, Centennial Park; John R. McCracken, Kareela, both of Australia

[73] Assignee: Unisearch Limited, Kensington, Australia

[21] Appl. No.: 949,528

[22] Filed: Oct. 10, 1978

[30] Foreign Application Priority Data

Oct. 10, 1977 [AU] Australia .............................. PD1987

[51] Int. Cl.[2] .................................................. C07J 9/00

[52] U.S. Cl. .................................................. 260/397.25

[58] Field of Search ..................................... 260/397.25

[56] References Cited

U.S. PATENT DOCUMENTS

| | | | |
|---|---|---|---|
| 2,772,297 | 11/1956 | Laquer | 260/397.25 |
| 3,526,647 | 9/1970 | Sunde et al. | 260/397.25 |
| 4,091,035 | 5/1978 | Clark | 260/397.25 |

*Primary Examiner*—Elbert L. Roberts

[57] ABSTRACT

A process for extracting valuable wool wax as a product having the specifications of lanolin from wool grease as found, for example, in the liquor from the scouring of raw wool. The process, apart from removing wool grease/wool wax from wool scouring effluent, avoids the production of pollutants in the extraction process, and in the case of the treatment of wet sludge containing wool grease produces a virtually grease-free solid product suitable for disposal as an environmentally safe soil.

11 Claims, 5 Drawing Figures

Figure 1:
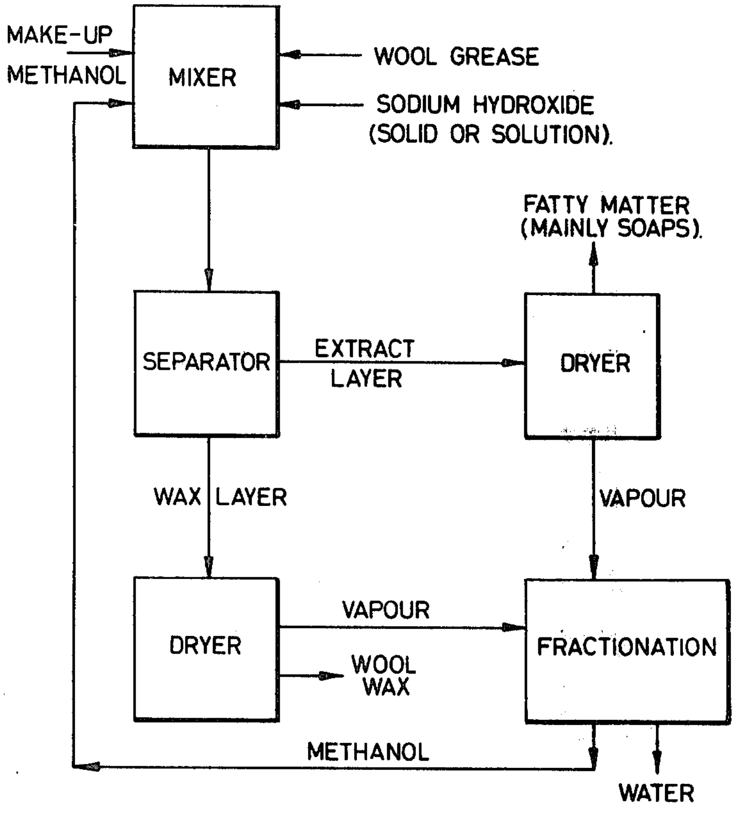

PROCESS FOR SEPARATION OF WOOL WAX FROM FATS IN WOOL GREASE OR MIXTURES CONTAINING WOOL GREASE

This invention relates to a process for extracting wool wax as a product approaching or having the specifications of lanolin, from fats and other impurities in partially dewatered sludge, centrifugally-recovered wool grease, solvent extracted wool grease, wool grease recovered by "acid-cracking" or by flotation, or obtained by any other process used for the treatment of liquor from the scouring of raw wool.

One object of the invention is to provide a simple process to efficiently separate most of the relatively valuable wool wax from the other components in wool grease or a mixture containing wool grease. Further objects are to avoid the production of pollutants in the extraction process and in the case of wet sludge to produce a virtually grease-free solid product suitable for disposal as an "environmentally safe" soil. Furthermore, the fats (all free fatty acids are converted to soaps) and other surface active matter removed in the final purification of the wool wax could be used in the scouring of raw wool or could find other outlets such as in the manufacture of various fatty products.

According to one aspect, the present invention provides a process for separation of wool wax from wool grease comprising heating the wool grease to above melting point, blending the molten wool grease with hot methanol, adding an alkali in an amount of about 120 percent of the calculated requirement for neutralization of the wool grease based on its acid value, separating the insoluble and immiscible wool wax layer from the methanol extract layer, and recovering the wool wax by conventional drying of said wool wax layer.

Thus according to this aspect of the invention there is provided a binary phase solvent extraction of molten wool wax from wool grease using methanol as the solvent, following reaction in a hot methanolic solution of an alkali (either of the hydroxides of potassium or sodium are suitable, the latter preferred) which mainly converts free fatty acids to soaps. The quantity of alkali required is about 20 percent in excess of that calculated from the acid value of the wool grease including that needed to neutralise any other components in the mixture not contributing to the wool grease content (e.g. a mineral acid). The soaps, together with other polar and surface active matters, transfer to the solvent phase since they have a greater affinity for methanol than for the wool wax. A countercurrent extraction is necessary if it is required to reduce the ash content of the wool wax-rich raffinate layer.

The alkali can be added either as a solid or as a methanolic or aqueous solution. If the acid value of the wool grease does not greatly exceed 1 mg KOH $g^{-1}$, or a countercurrent extraction is not required, then an alkalkine methanolic solution would be most practicable since less water has to be removed from the methanol and the mass ratio of methanol to wool grease can be kept low (e.g. 1:1) avoiding extensive distillation for methanol recovery. However, for most wool greases it would be preferable to use a concentrated aqueous solution of alkali (e.g. 50% w/v sodium hydroxide) because (i) the acid value is considerably greater than unity meaning large volumes of methanol have to be used to dissolve sufficient alkali to lower the acid value of the wool wax to about unity or lower (ii) a countercurrent extraction will be required to reduce the ash content of the wool wax raffinate and this will usually be achieved best by using all of the methanol for extraction rather than diverting much of the methanol to dissolving alkali where it is used in the first stage's (nearest to the feed of wool grease) of the extraction train, (iii) water will have to be stripped from the methanol anyway since water is liberated in the conversion of fatty acids to soaps, the wool grease may not be completely dry and/or water will be added during a bleaching operation with, say, a concentrated aqueous solution of hydrogen peroxide, prior to extraction with methanol. Alternatively, it may prove to be of considerable advantage to add the concentrated aqueous solutions of alkali and hydrogen peroxide to the wool grease in a separate mixing vessel; i.e. in a premixing stage, for bleaching (since optimum performance with hydrogen peroxide occurs at about pH 10) prior to passing the mixture to the last stage of the methanol extraction train. In this way the whole of the extraction unit is used for extraction (and not partly for reaction) and both the wool wax and fatty matter products are bleached and no further water removal operations are necessary as would be the case if bleaching was carried out after the methanol extraction.

According to another aspect the present invention provides a process for extracting wool grease from an aqueous mixture containing wool grease (in which the soaps have been converted to fatty acids) prior to separation of wool wax from said wool grease, comprising co-distillation of said aqueous mixture with a water-immisscible lipid solvent to remove most of the water, removal of solvent-insoluble solids or coagulated material from the solvent solution of lipids by conventional means, separating the condensed solvent and aqueous layers, recycling the solvent for codistillation, and recovering the lipids/solvent by conventional drying of said solvent solution of lipids.

According to this aspect the wool grease is first extracted from an emulsion or a wet sludge in which all soaps have been converted to fatty acids, prior to the alkaline methanolic extraction for the recovery of wool wax, whereby lipids are separated from the other components of the mixture, including, in particular, colloidal particles of clay and other solid matter which usually pose considerable problems in their removal. This is achieved with a solvent having certain suitable properties, by first co-distilling off most of the water and then separating the dissolved lipids from the solvent by distillation. The solid components which settle out during the water removal stage are removed from the solution and stripped of most of the adhering solvent, prior to their disposal. Removal of the water from a mixture of lipids containing wool grease by co-distillation with a suitable solvent appears to cause all of the solid particles to coagulate within the solution of lipids in solvent and prevents the usual problem of colloidal particles remaining in the wool grease and ultimately in the wool wax product. The coagulation of solids permits their removal from the solution of lipids in solvent without difficulty either by filtration, straining, decantation, centrifuging, etc. The solvent remaining in this solid mass can be removed either by stripping with steam (preferred method) or vacuum extraction or similar conventional processes. The most desirable properties of the solvent are water-immiscibility and a relatively low boiling point. Being water-immiscible the solvent will immediately separate from the water stripped from the feed mixture containing wool grease after the vapours are condensed. The solvent can then be recycled to the distilling apparatus. A relatively low boiling point solvent is required to avoid scorching of certain components in the wool grease most pronounced at temperatures above 100° C. and/or when heating for prolonged periods. It may be considered an advantage to vacuum distil off the water with the solvent to further lower the operating temperature. Trichloroethylene has been found to be a suitable solvent for rapid co-distillation at atmospheric pressure and has the added advantage that it is a relatively cheap solvent, is not flammable and has a low toxicity rating.

Since a trace amount of the water-immiscible solvent, such as trichloroethylene, usually remains in the water following the stripping and/or co-distillation stages of recovering lipids from an emulsion or wet sludge, it may prove difficult to dispose of this water to the environment. A further part of this invention comprises one method for safely disposing of this water by raising steam from it in a boiler and using this steam for stripping the solvent from the sludge solids. The vapours from the steam stripping operation can then be condensed with the vapours from the co-distillation operation to separate the water from the solvent. The excess steam produced in this way, the weight of which is the balance between the water carried in with the greasy sludge and the water carried away with the grease-free soil. can then be passed through the combustion zone of the boiler to incinerate the entrained trace of solvent. Passing steam into the combustion zone of the boiler can be used to advantage for better atomisation of the fuel, particularly when a viscous, cheap fuel is available. However, the amount of steam that can be passed through the combustion zone of a boiler is relatively small (e.g. not greater than 10 percent of the fuel) and this method is therefore limited to operations where a large capacity boiler is employed for other purposes and/or where only a small quantity of water is carried into the process with the wool grease.

The invention will be further described with reference to process-flow diagrams, FIGS. 1 to 5, which are included, by way of example, to illustrate various means of operation of the invention.

FIG. 1: Molten wool grease is blended in a mixing vessel with hot methanol and sodium hydroxide (either as a solid or solution, preferably as a methanolic solution) added at a rate of about 120 percent of the calculated requirement for neutralisation of the wool grease based on its acid value. The mixture is then passed to a separator where insoluble wool wax will separate from a methanol extract containing mainly fatty matter as soaps and some water. Both the wool wax and fatty matter extract layers are sent to dryers (such as thin film evaporators) where methanol and water are removed as vapours to be recovered separately by fractionation, and the methanol is recycled to the mixing vessel. Of course, if the wool grease was not dry because it had been bleached prior to this process or bleach was also added into the mixing vessel as, say, a concentrated solution of hydrogen peroxide and/or the wool grease had been recovered as an emulsion and/or the sodium hydroxide had been added as an aqueous solution, then more water than liberated by reaction of the fatty acids with sodium hydroxide to form soaps (i.e. 0.45 kilogram water liberated per kilogram sodium hydroxide used) would have to be removed by the fractionation process.

Since the solubility of wool grease in methanol is dependent on its concentration, being particularly more soluble at lower values, it is necessary to use a high concentration of wool grease in methanol to minimise the proportion of wool wax extracted along with fatty and other matter. Apart from improving the yield of wool wax, a high concentration (e.g. one kilogram of wool grease per kilogram of methanol) also results in a lower energy requirement for evaporating methanol in the solvent recovery operation. However, a high concentration will also result in a higher ash concentration in the wool wax which is particularly relevant when the acid value of the wool grease is high (i.e. significantly above 1 mg KOH $g^{-1}$). Therefore, in this case it is necessary to establish the minimum concentration of wool grease in methanol from the maximum permissible concentration of ash in the wool wax product, but in any event, will not likely be less than about one kilogram of wool grease per kilogram of methanol due to physical handling and separation limitations.

Figure 2:
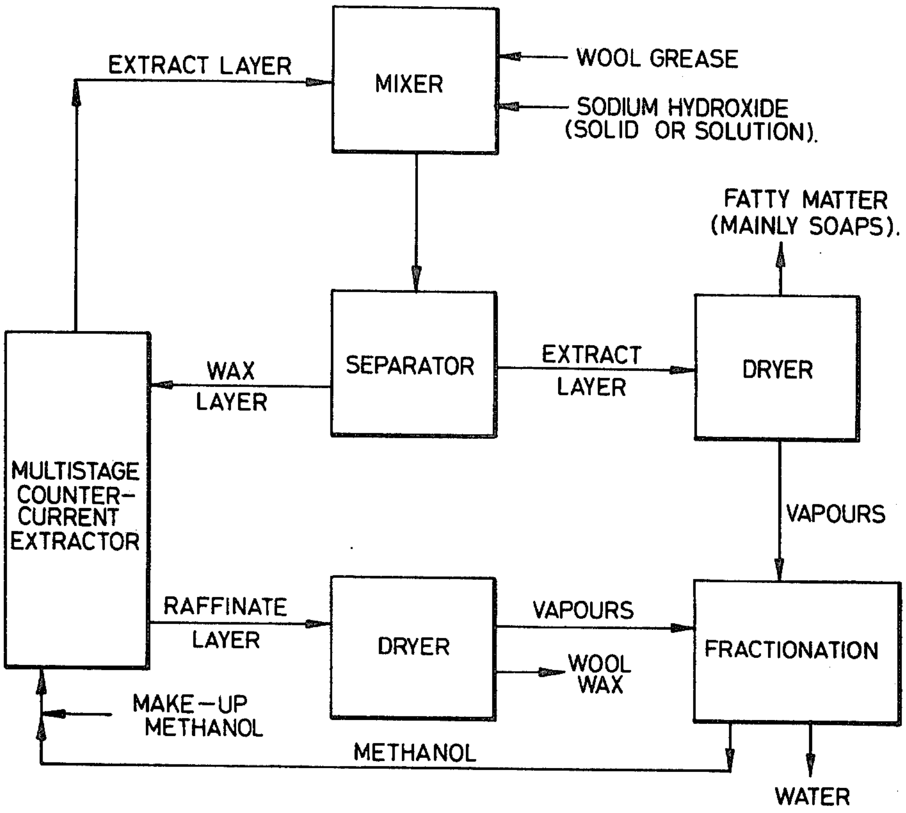
Figure 3:
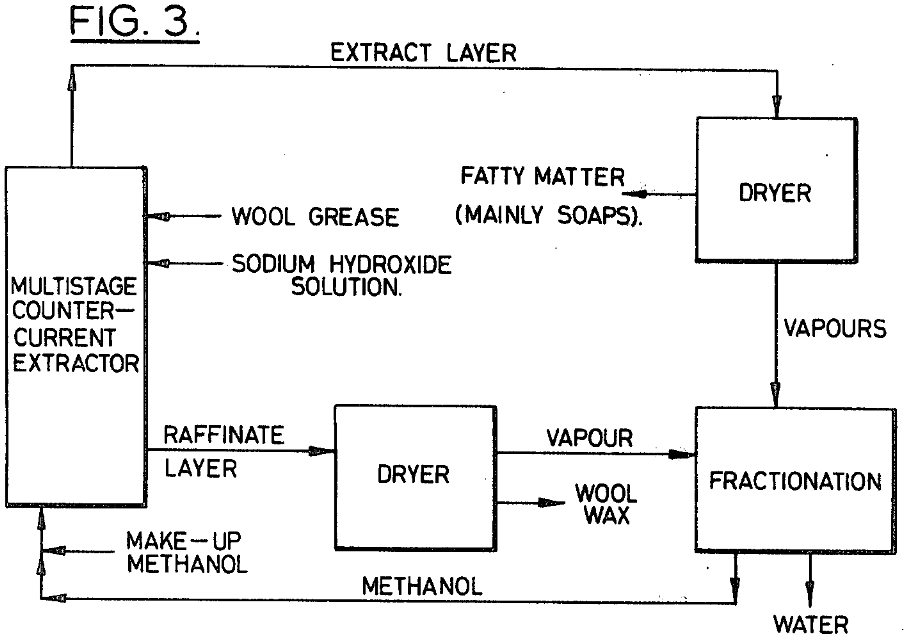
Figure 4:
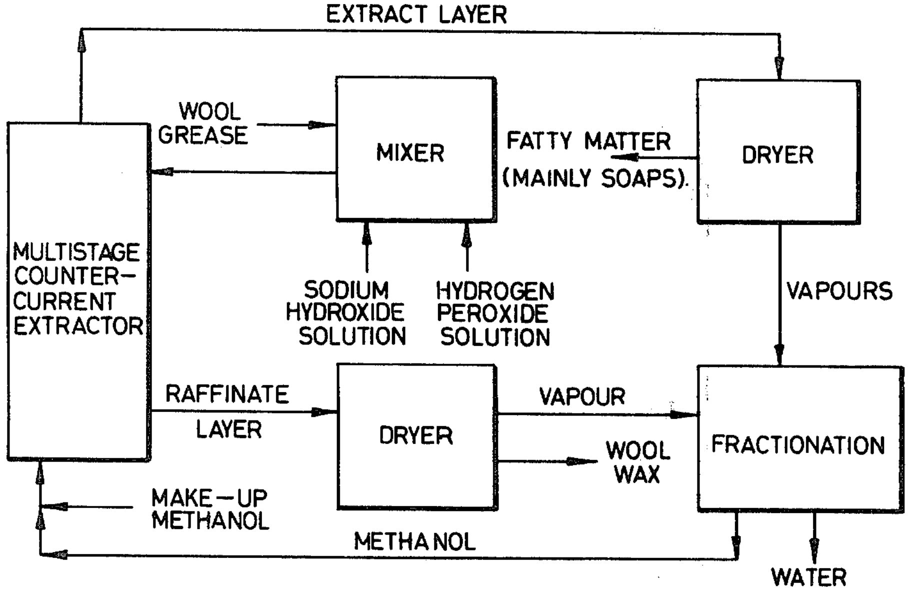

FIGS. 2, 3 and 4: If a low ash content is required in the wool wax (e.g. less than 0.15 percent by weight as required in the British Pharmacopaeia specification for lanolin) then a multistage countercurrent extraction of the neutralised wool grease with methanol will be required. FIG. 2 illustrates means whereby the bulk of the methanol-soluble matter is removed from the wool grease by the same method as shown in FIG. 1, external to the countercurrent extraction and would normally be used where the wool content of the wool grease was low (i.e. significantly less than 50 percent) and/or where the addition of water into the system is to be restricted (the alkali then being added as a solid). FIG. 3 illustrates means whereby the whole of the extraction and neutralisation operations are performed in the countercurrent extraction machine and would normally be used (i) where the acid value of the wool grease was very low in which case a relatively small amount of the methanol being used could be diverted to make a concentrated solution of sodium hydroxide to be introduced at an appropriate intermediate extraction stage (e.g. a wool grease having an acid value of 3 mg KOH $g^{-1}$ would require the diversion of only 12.6 percent of the methanol being used for a countercurrent extraction rate of one kilogram of wool grease to one kilogram of methanol to make up a 2 percent methanolic solution of sodium hydroxide supplied at a rate of 120 percent of the calculated requirement for neutralisation), or (ii) where the acid value is large, but the wool wax content is also large, requiring the introduction of a concentrated aqueous solution of sodium hydroxide to be introduced at an appropriate intermediate extraction stage (e.g. a wool grease having an acid value of 20 mg KOH $g^{-1}$ and a 50 percent wool wax content would require 34.3 grams of a 50 percent aqueous solution of sodium hydroxide per kilogram of wool grease when supplied at a rate of 120 percent of the calculated requirement for neutralisation and this is only 3.4 percent of the mass of methanol being used for a countercurrent extraction rate of one kilogram of wool grease to one kilogram of methanol or equivalent to one kilogram of wool wax to two kilograms of methanol). FIG. 4 illustrates the most preferred means whereby the neutralisation and bleaching operations are carried out in a mixing vessel prior to extraction with methanol (e.g. as shown in any of FIGS. 1, 2 or 3).

Figure 5:
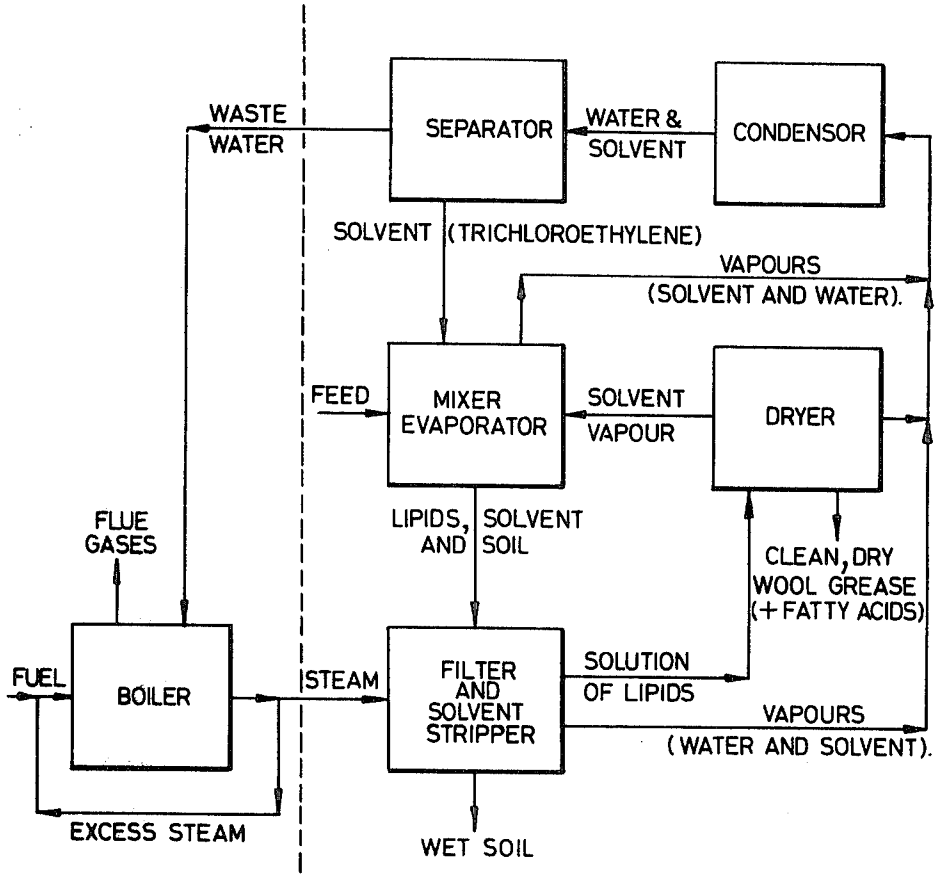

FIG. 5: When the wool grease is contained in a wet sludge (e.g. containing about half its weight as water and equal proportions of wool grease and soil—fairly typical of sludge produced by a physico-chemical treatment of waste wool scouring liquor) or in an emulsion (e.g. containing 30 percent water in wool grease as might be produced by centrifuging a wool scouring liquor) and particularly when in the presence of colloidal particles of soil material, then it will usually be necessary to free the wool grease of this matter prior to a methanolic extraction for the recovery of wool wax. This can be achieved by first removing most of the water by co-distillation with a suitable solvent (e.g. trichloroethylene, distilled at a minimum rate of between 11-15 kilograms per kilogram of water contained in the emulsion or wet sludge) in a machine such as an evaporator (vacuum operation optional) providing adequate agitation to the mixture. It is important that all soaps in the feed material have been converted to fatty acids prior to this process (which can be effected by heating with a mineral acid in the presence of water) in order that they will dissolve in the solvent with the wool grease and not form gelantinous masses which soaps have the tendency to do in mixtures of this nature. The vapours are condensed and the water-immiscible solvent separates almost completely from the water. The solvent-insoluble components of the mixture tend to coagulate and are easily removed from the solution of lipids in solvent by filtration. The solvent remaining in these solids after a solvent washing operation is stripped by steam preferably in-situ in the filter and the vapours are sent back to the condensor and separator for recovery of solvent and water. The moist greasefree solids are then ready for disposal as landfill, etc. (Laboratory filtration data indicates that the optimum dry solids surface loading on a filter is in the vicinity of 10 kg $m^{-2}$ when the quantity of steam required to completely strip trichloroethylene is a minimum of about 0.5 kilogram of steam per kilogram of dry solids. Also, the residual water in the sludge after steam stripping is not likely to exceed 30 percent of the weight of dry solids and the volume of the moist sludge is increased by about 15 percent over the dry settled volume). The solution of lipids in solvent is passed to a dryer (e.g. a thin film evaporator) to separate solvent and wool grease. The solvent vapour can be passed directly to the condensor or, preferably, passed countercurrently through the mixture in the mixer-evaporator to force a greater rate of evaporation of water by increasing the concentration of solvent in the vapour phase beyond the equilibrium value. The wool grease obtained in this way is then in a suitable condition for an alkaline methanolic extraction for wool wax. The waste water produced by the process is likely to contain some solvent which could cause a disposal problem (e.g. the solubility of trichloroethylene in water at 25° C. is 1 g $l^{-1}$). To avoid this problem, the waste water can be passed to a boiler to generate steam for various purposes including the operation of stripping solvent from the solids retained by the filter. The excess steam, the weight of which is the balance of the water carried in with the feed material containing wool grease less the water carried away with the grease-free sludge, is used to assist atomisation of the fuel in the combustion zone of the boiler and the entrained solvent is thus destroyed.

What we claim is:

1. A process for separation of wool wax from wool grease comprising heating the wool grease to above melting point, blending the molten wool grease with hot methanol, adding an alkali in an amount of about 120 percent of the calculated requirement for neutralization of the wool grease based on its acid value, separating the insoluble and immiscible wool wax layer from the methanol extract layer, and recovering the wool wax by drying of said wool wax layer.

2. A process according to claim 1, wherein said wool wax layer is subjected to countercurrent extraction prior to drying of said layer.

3. A process according to claim 1, wherein neutralization of the wool grease with alkali and separation of the wool wax layer from the methanol extract layer is effected simultaneously in a multi-stage countercurrent extractor apparatus.

4. A process according to claim 3, wherein neutralization of the wool grease with alkali is carried out simultaneously with bleaching of the wool grease with hydrogen peroxide in a premixing stage prior to addition to the countercurrent extraction apparatus.

5. A process according to claim 1, wherein the methanol extract layer is dried to recover solids therefrom.

6. A process according to claim 5, wherein vapours from the drying of both the wool wax layer and the methanol extract layer are fractionated to recover methanol and water.

7. A process according to claim 6, wherein the methanol is recycled for a continuous extraction process.

8. A process according to claim 1, wherein said alkali is either sodium hydroxide or potassium hydroxide.

9. A process according to claim 1 wherein said alkali is added either as a solid or as a concentrated aqueous or a methanolic solution.

10. A process for extracting wool grease from an aqueous mixture containing wool grease (in which the soaps have been converted to fatty acids) prior to separation of wool wax from said wool grease, comprising co-distillation of said aqueous mixture with a water-immiscible lipid solvent to remove most of the water, removing solvent-insoluble solids or coagulated material from the solvent solution of lipids, separating the condensed solvent and aqueous layers, recycling the solvent for codistillation, and recovering the lipids/solvent by drying of said solvent solution of lipids.

11. A process according to claim 10, wherein said water-immiscible lipid solvent is trichloroethylene.

* * * * *